United States Patent [19]

O'Neill

[11] Patent Number: 5,196,600
[45] Date of Patent: Mar. 23, 1993

[54] SYNTHESIS OF FLUORINATED DIMETHYL ETHERS

[75] Inventor: Gerald J. O'Neill, Arlington, Mass.

[73] Assignee: W. R. Grace & Co.-Conn., New York, N.Y.

[21] Appl. No.: 858,387

[22] Filed: Mar. 25, 1992

[51] Int. Cl.$^5$ .................... C07C 43/12; C07C 41/22
[52] U.S. Cl. .................... 568/684; 568/681; 568/683
[58] Field of Search ............... 568/613, 614, 615, 681, 568/683, 684

[56] References Cited

U.S. PATENT DOCUMENTS 3,461,213  8/1969  Terrell ........................... 568/684
3,896,178  7/1975  Terrell ........................... 568/683

FOREIGN PATENT DOCUMENTS 949978  6/1974  United Kingdom ............... 568/684

OTHER PUBLICATIONS

Parks et al, "J. Amer. Chem. Soc." vol. 76 (1954) pp. 1387–1388.
Parks et al "J. Amer. Chem. Soc." vol. 74 (1952) pp. 2292–2293.

Primary Examiner—Werren B. Lone
Attorney, Agent, or Firm—John Dana Hubbard; William L. Baker

[57] ABSTRACT

A novel process is disclosed for the synthesis of fluorinated dimethyl ethers of the formula $CF_2HOCCl_xF_yH_{3-(x+y)}$ wherein x is 0, 1 or 2; y is 1, 2 or 3; and wherein the total $x+y$ is 1, 2 or 3. The process involves chlorination of methyl difluoromethyl ether to form a chlorinated reaction product, including at least one compound of the formula $CF_2HOCH_{3-z}Cl_z$, wherein z is 1, 2 or 3, which compound is then fluorinated with HF and/or an antimony salt and with or without separation from the chlorinated reaction product, to give a fluorinated reaction product including the aforementioned fluorinated dimethyl ethers.

22 Claims, No Drawings

SYNTHESIS OF FLUORINATED DIMETHYL ETHERS

FIELD OF THE INVENTION

This invention relates to a process for the synthesis of the fluorinated dimethyl ethers which have utility as refrigerants, etc.

BACKGROUND OF THE INVENTION

Bis(difluoromethyl) ether has been prepared previously by chlorination of dimethyl ether followed by isolation and fluorination of bis(dichloromethyl)ether. The chlorination step gave a complex mixture of chlorinated dimethyl ethers some of which were unstable, e.g. to distillation, from which bis(dichloromethyl)ether was separated. Two of the ethers in the mixture, chloromethyl methyl ether and bis(chloromethyl)ether, are potent carcinogens.

Due to the difficulty and cost in preparing dimethyl ether products which are free of carcinogens, little effort has been focused on their synthesis. This is especially true in view of the well known, commercially available alternatives, such as "FREON" "HALON" and other well known chlorofluorocarbons (CFCs) which are used as refrigerants, etc.

However, the use of CFCs has been sharply curtailed and will eventually be phased out due to their propensity to destroy the ozone layer.

The use of bis(difluoromethyl)ether has been proposed as a propellant and as a refrigerant alternative to CFCs. See U.S. Pat. Nos. 4,041,148 and 4,961,321. The known processes for forming such alternatives are too expensive, have too low a yield and generate harmful (carcinogenic) byproducts, making the development of inexpensive CFC alternatives unlikely.

There is a critical need for the discovery and commercialization of practical, economical processes for the production of alternative environmentally safe compounds to replace the CFCs.

SUMMARY OF THE INVENTION

It is an object of the present invention to provide a process for synthesis of fluorinated dimethyl ethers which does not produce carcinogens as intermediates.

Another object of the present invention is to provide a process for synthesis of fluorinated dimethyl ethers wherein the various required separations may be effected by distillation without loss of yield and danger of explosion due to marked instability of the various intermediates.

The unstable complex mixture of chlorinated ethers, some of which are carcinogens, in accordance with the prior art, is avoided in the present invention by employing methyl difluoromethyl ether as a starting material. The methyl difluoromethyl ether is chlorinated to give a chlorinated reaction mixture including at least one compound of the formula $CF_2HOCH_{3-z}Cl_z$, wherein z is 1, 2, or 3, which compound can readily be separated from the chlorinated reaction mixture. The chlorination of methyldifluoromethyl ether would generally form only three derivatives, i.e. z=1, z=2 and z=3. The dichloromethyl difluoromethyl ether (z=2) can readily be separated from the chlorinated reaction mixture and is then fluorinated, with or without such separation, to form the bis(difluoromethyl)ether. $CF_2HOCCl_3$ (z=3) may also be separated from the chlorination reaction product and fluorinated. Alternatively, the chlorination reaction product itself may be fluorinated (without prior separation) as follows:

  (I)

  (II)

  (III)

All of the above would find utility as refrigerants, especially (I) monofluoromethyl difluoromethyl ether and (II) bis(difluoromethyl)ether, which are considered to be substitutes for R-11 and R-114 refrigerants, respectively and (III) difluoromethyl trifluoromethyl ether. This compound is being considered as a refrigerant replacement for R-12 and also R-22.

The chlorination and fluorination steps of the present invention may be represented as follows:

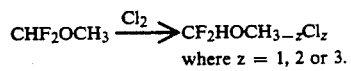

where z = 1, 2 or 3.

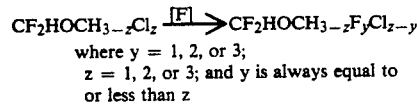

where y = 1, 2, or 3;
z = 1, 2, or 3; and y is always equal to or less than z

DESCRIPTION OF PREFERRED EMBODIMENTS

The methyl difluoromethyl ether which is regarded as the starting material for the process of the present invention is a known compound which may be prepared in the manner reported by Hine and Porter in their article published in the *Journal of the American Chemical Society*. See "Methylene derivatives as intermediates in polar reactions. VIII. Difluoromethylene in the reaction of chlorodifluoromethane with sodium methoxide." Jack Hine and John F. Porter, *J. Am. Chem. Soc.* 79, 5493–6 (1957), the teachings of which are incorporated herein by reference. In their article Hine and Porter describe the production of difluoromethyl methyl ether ($CHF_2OCH_3$) by reaction of sodium methoxide (NaOMe) with chlorodifluoromethane ($CF_2HCl$), which reaction may be represented as follows:

Briefly, the method involves forming an alcohol solution of sodium methoxide and bubbling the chlorodifluoromethane slowly into the reaction mixture to obtain the methyldifluoromethyl ether as a residue in the reaction mixture. Some product is entrained with unreacted $CF_2HCl$ and can be separated from it in a distillation operation.

The starting ether, $CHF_2OCH_3$, might also be prepared by first reacting NaOH with $CH_3OH$, in effect making $CH_3ONa$, and then reacting it with $CF_2HCl$. However, water is also formed in the $NaOH/CH_3OH$ reaction. The effect the water has on the subsequent reaction to form $CHF_2OCH_3$ is to reduce the yield of $CHF_2OCH_3$.

In accordance with the present invention, methyldifluoromethyl ether is chlorinated as follows:

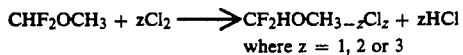
$$CHF_2OCH_3 + zCl_2 \longrightarrow CF_2HOCH_{3-z}Cl_z + zHCl$$
where $z = 1, 2$ or $3$ It has been found that the $CHF_2OCH_3$ may suitably be chlorinated by liquifying the $CHF_2OCH_3$ and reacting it with chlorine gas while irradiating with a source of visible light. Alternatively, one may use other light sources such as ultraviolet light or heat, a catalyst or a free radical initiator to aid in the reaction. The chlorination products of $CHF_2OCH_3$ can be readily separated prior to fluorination or the reaction mixture can be fluorinated without separation to give an admixture of $CF_2HOCCl_2F$, $CF_2HOCF_2Cl$, $CF_2HOCH_2F$, $CF_2HOCFHCl$, $CF_2HOCF_2H$ and $CF_2HOCF_3$. All separations may be effected by fractional distillation.

A preferred method of chlorinating the $CHF_2OCH_3$ is to maintain the $CHF_2OCH_3$ in a vapor phase and react it with chlorine gas while subjecting the chlorination reaction to a source of light, preferably visible or ultraviolet light. Alternatively, other reaction aids such as a catalyst, heat or a free radical initiator may be used instead of light in the chlorination reaction. The chlorination reaction only forms the three derivatives discussed above, which can be separated prior to fluorination or not, as discussed above.

One method found suitable for the fluorination of the chlorination reaction product involves reaction of the halogenated dimethylether or ethers with antimony trifluoride. The reaction may be represented as follows:

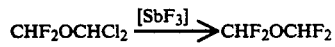
$$CHF_2OCHCl_2 \xrightarrow{[SbF_3]} CHF_2OCHF_2$$

On an industrial scale the antimony trifluoride reaction can be carried out in a continous mode by a continuous regeneration of the catalyst with HF. This is done by using a mixture of $SbF_3$ and chlorine to give the pentavalent salt $SbF_3Cl_2$, or on a small scale it can be done by using a mixture of $SbF_3$ and $SbCl_5$, as in the examples which follow. More commonly, antimony pentachloride alone is used as follows:

$$SbCl_5 + yHF \longrightarrow SbCl_{(5-y)}Fy + yHCl$$

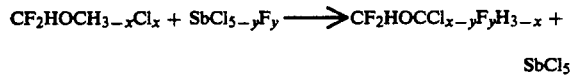
$$CF_2HOCH_{3-x}Cl_x + SbCl_{5-y}F_y \longrightarrow CF_2HOCCl_{x-y}F_yH_{3-x} + SbCl_5$$

The mixed salt catalyst, likewise, may be continuously regenerated by the addition of HF.

In the preferred fluorination procedure the chlorinated reaction product is reacted with anhydrous hydrogen fluoride (HF), which reaction may be represented as follows:

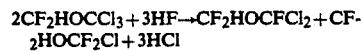
$$2CF_2HOCCl_3 + 3HF \rightarrow CF_2HOCFCl_2 + CF_2HOCF_2Cl + 3HCl$$

Utilizing the above reaction with hydrogen fluoride the inventor has obtained a yield as high as 78% $CF_2HOCF_2Cl$ with a small amount of $CF_2HOCFCl_2$. This was an unexpected result since HF by itself does not normally replace a halogen such as chlorine, except perhaps at very high temperatures, but instead fluorinates by continuous regeneration of a fluorinating agent such as $SbCl_{5-y}F_y$, such as $SbF_3$, or $SbF_3Cl_2$. Apparently, the difluoromethyoxy group activates the chlorine on the alpha-carbon atom allowing it to react readily with HF.

Alternatively, the HF may be diluted with an organic solvent, preferably a dipolar aprotic solvent such as methyl pyrrolidone, in order to reduce fragmentation of the fluorinated material, resulting in higher yields of desired products with less byproducts generation.

The resultant fluorinated products may be separated by distillation or by the process as taught in U.S. Pat. No. 4,025,567 or U.S. Pat. No. 3,887,439 which are incorporated herein in their entirety.

The present invention will now be further illustrated by the following examples.

EXAMPLE 1 a) Preparation of $CF_2HOCH_3$

A 25 wt % solution of sodium methoxide in methanol (1533.1 g) containing 7.1 moles of sodium methoxide was placed in a 4 liter jacketed autoclave fitted with temperature sensor, a pressure gauge and a dipleg. The vessel was cooled to 0° to 5° C. and chlorodifluoromethane a period of 2.5 hours with agitation. When the addition of gas had been completed, the autoclave was slowly warmed to about 60° C. while venting gaseous products through the water-cooled condenser into a collection trap cooled to about −70° C.

When all volatile material had been collected unreacted $CHF_2Cl$ was removed at −20° C. and the remaining $CF_2HOCH_3$ transferred to a metal cylinder. The recovered difluoromethyl methyl ether (150.0 g, 1.83 moles) represented a yield of 49.4% based on $CF_2HCl$.

b) Chlorination of $CF_2HOCH_3$

Chlorine and $CHF_2OCH_3$ in a gaseous phase are passed through separate condensers cooled to 0° C. and then the gas streams combine and pass into one arm of a U-shaped reactor, irradiated with visible light or UV. Both arms of the reactor are jacketed and cooled with water.

There is an outlet at the bottom of the U to which is attached a product collection flask. A Dewar-type condenser cooled to −50° C. is attached to the outlet of the second arm of the U-tube and, in turn, it is connected in series with a cold trap to collect unreacted chlorine and an NaOH scrubber to remove HCl. The reaction is normally carried out at atmospheric pressure, but higher or lower pressure can be used. Temperature should not be allowed to rise much above 50° C. in the reactor to avoid attack on the glass.

In practice, the apparatus is flushed with nitrogen and then chlorine and $CHF_2OCH_3$ are fed to the reactor at rates such that the ratio of the flow of chlorine to that of the ether is maintained at about 2.5:1 for optimum results, i.e., yield of $CF_2HOCHCl_2$. A predominant amount of any one of the three products can be obtained by changing the ratio of the gas flows.

After the passage of 2.3 moles of chlorine and 0.9 mole of $CHF_2OCH_3$, 136.6 g of product were recovered. GC analysis of the product mixture showed CF$_2$HOCH$_2$Cl 10.0%, CF$_2$HOCHCl$_2$, 62.4% and CF$_2$HOCCl$_3$ 22.2%.

c) Fluorination of CHF$_2$OCHCl$_2$ with SbF$_3$.

Antimony trifluoride (9.8 g) and CF$_2$HOCHCl$_2$ (24.9 g) were placed in a 50 ml, 3-necked, round bottomed flask fitted with a thermometer, a magnetic stirrer and a water condenser connected in series with a cold trap. The mixture was stirred for ½ hour then heated to 57° C. for 15 minutes.

GC analysis of the material recovered from the cold trap shows it to contain 64.3% CHF$_2$OCHF$_2$, a yield of 62.5%. The other product of the reaction, CHF$_2$OCHFCl, accounted for 26.5% of the product mixture.

d) Alternative Fluorination of CHF$_2$OCHCl$_2$ with HF.

Alternatively, the chlorinated CHF$_2$OCH$_3$ (40.0 g) containing 46.1% CF$_2$HOCHCl$_2$ in a stainless steel cylinder which was then cooled in ice before adding anhydrous HF (30.0 g). The cylinder was closed with a valve and pressure gauge and then was placed in a water bath at 60° C. for 3 hours. The cylinder was then vented through a NaOH scrubber and volatile products collected in a trap cooled at −70° C. The weight of product recovered from the trap was 16.8 g. It contained 71.8% CF$_2$HOCF$_2$H by GC analysis, corresponding to a yield of 83.8% of CF$_2$HOCF$_2$H.

EXAMPLE 2

SbF$_3$ (74. g) and SbCl$_5$ (0.75 g) were placed in a 50 ml 3-necked, round bottom flask fitted with a thermometer, a magnetic stirrer and a water condenser connected in series with a cold trap. A sample of chlorinated difluoromethyl ether (13. g), containing 9.4% CF$_2$HOCH$_2$Cl, 29.1% CF$_2$HOCHCl$_2$, and 51.1% CF$_2$HOCCl$_3$, was slowly added to the stirred mixture. The temperature of the reaction system rose to 44° C. without the application of heat. GC analysis of the recovered product (9.2 g) showed it to consist of CF$_2$HOCF$_2$H (27.0%), CF$_2$HOCF$_2$Cl (38.5%), and CF$_2$HOCFCl$_2$ (21.9%).

EXAMPLE 3

Preferred fluorination step

A sample of chlorinated difluoromethyl ether mixture (25 gm) containing 50% CF$_2$HOCCl$_3$, was placed in a polyethylene flask fitted with an inlet tube for nitrogen as carrier gas, an outlet tube leading to a second polyethylene flask containing NaOH solution (10%), followed by a drying tube and a trap cooled in Dry Ice/MeOH.

An excess of anhydrous hydrogen fluoride was added to the chlorinated ether and the mixture stirred with a magnetic stirrer. Heat was not applied, the temperature remaining at about 20° C. More hydrogen fluoride was added to the mixture as needed until all the organic material had reacted. The weight of material collected from the cold trap was 9.5 g.

Analysis of the recovered product by GC showed it to consist of 84.3% CF$_2$HOCF$_2$Cl, a yield of 78% based on the CF$_2$HOCCl$_3$ content of the chlorinated mixture. A small amount of CF$_2$HOCFCl$_2$ was also present.

The above examples are representive and the invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims and therefore intended to be embraced therein.

I claim:

1. A process for the preparation of fluorinated dimethyl ethers of the formula CF$_2$HOCCl$_x$F$_y$H$_{3-(x+y)}$, wherein x is 0, 1 or 2 and y is 1, 2 or 3 and wherein the total x+y is 1, 2 or 3, said process comprising:

chlorinating CHF$_2$OCH$_3$ by reacting said CHF$_2$OCH$_3$ with chlorine to form a chlorinated admixture containing at least one compound of the formula CF$_2$HOCH$_{3-z}$Cl$_z$, wherein z is 1, 2 or 3; and fluorinating said at least one compound of the formula CF$_2$HOCH$_{3-z}$Cl$_z$, with hydrogen fluoride in the absence of a catalyst to obtain a fluorinated admixture containing at least one compound of a formula CF$_2$HOCH$_{3-z}$F$_y$Cl$_{z-y}$.

2. A process in accordance with claim 1 wherein said chlorination step occurs in either a vapor or liquid phase and the chlorine is in the form of a liquid or a gas.

3. A process in accordance with claim 2 wherein said chlorination step is in the vapor phase and the chlorine is in the form of a gas.

4. A process in accordance with claim 1 wherein the hydrogen fluoride is selected from the group consisting of anhydrous hydrogen fluoride and hydrogen fluoride in an organic solvent.

5. A process in accordance with claim 1 wherein said at least one compound of the formula CF$_2$HOCH$_{3-z}$Cl$_z$ is CF$_2$HOCHCl$_2$ and said fluorinated reaction product includes CF$_2$HOCF$_2$H and CF$_2$HOCHFCl.

6. A process in accordance with claim 1 wherein said at least one compound of the formula CF$_2$HOCH$_{3-z}$Cl$_z$ is CHF$_2$OCHCl$_2$ and said at least one compound of the formula CF$_2$HOCCl$_x$F$_y$H$_{3-(x+y)}$ is CHF$_2$OCHF$_2$ and further comprising separating and recovering said CHF$_2$OCHF$_2$ from said fluorinated admixture.

7. A process in accordance with claim 1 wherein said at least one compound of the formula CF$_2$HOCH$_{3-z}$Cl$_z$ is CF$_2$HOCCl$_3$, and said at least one compound of the formula CF$_2$HOCCl$_x$F$_y$H$_{3-(x+y)}$ is selected from the group consisting of CF$_2$HOCF$_2$Cl and CF$_2$HOCFCl$_2$ and further comprising separating and recovering said CF$_2$HOCF$_2$Cl and/or CF$_2$HOCFCl$_2$ from said fluorinated mixture.

8. A process in accordance with claim 7 wherein said fluorinating involves reacting said CF$_2$HOCCl$_3$ with anhydrous HF.

9. A process in accordance with claim 1 wherein said chlorination is conducted at a temperature and pressure sufficient to maintain said CF$_2$HOCH$_3$ in a gaseous state.

10. A process in accordance with claim 1 further comprising reacting CHF$_2$Cl with an alkali metal methoxide in solvent solution to form said CHF$_2$OCH$_3$.

11. A process in accordance with claim 6 wherein an admixture of CF$_2$HOCH$_3$ and CHF$_2$Cl is subjected to said chlorinating.

12. A process in accordance with claim 1 wherein the hydrogen fluoride is is hydrogen fluoride diluted with an organic solvent.

13. The process of claim 1 further comprising the chlorination step occurs in the presence of a reaction aid.

14. The process of claim 13 wherein the reaction aid is selected from the group consisting of light, heat, catalysts and free radical initiators.

15. A process for the preparation of fluorinated dimethyl ethers of the formula $CF_2HOCCl_xF_yH_{3-(x+y)}$, wherein x and y are each independently 0, 1, 2 or 3 and wherein the fluorination comprises reacting at least one compound of the formula $CF_2HOCH_{3-z}Cl_z$ with hydrogen fluoride in the absence of a catalyst.

16. A process in accordance with claim 15 wherein the hydrogen fluoride is in anhydrous form.

17. A process in accordance with claim 15 wherein the hydrogen fluoride is diluted with an organic solvent.

18. A process for the process for the preparation of fluorinated dimethyl ethers of the formula $CF_2HOCCl_xF_yH_{3-(x+y)}$, wherein x and y are each independently 0, 1, 2 or 3 and wherein the fluorination comprises reacting at least one compound of the formula $CF_2HOCH_{3-z}Cl_z$ wherein z is 1, 2 or 3; with hydrogen fluoride diluted in an organic solvent.

19. The process of claim 18 wherein the fluorination of $CF_2HOCH_{3-z}Cl_z$ with the hydrogen fluoride occurs in the absence of a catalyst.

20. The process of claim 18 wherein the organic solvent is an aprotic solvent.

21. The process of claim 20 wherein the solvent is methyl pyrrolidone.

22. A process for the preparation of fluorinated dimethyl ethers of the formula $CF_2HOCCl_xF_yH_{3-(x+y)}$, wherein x is 0, 1 or 2 and y is 1, 2 or 3 and wherein the total x+y is 1, 2 or 3, said process comprising:

chlorinating $CHF_2OCH_3$ by reacting said $CHF_2OCH_3$ with chlorine to form a chlorinated admixture containing at least one compound of the formula $CF_2HOCH_{3-z}Cl_z$, wherein z is 1, 2 or 3; and fluorinating said at least one compound of the formula $CF_2HOCH_{3-z}Cl_z$, with hydrogen fluoride in the absence of a catalyst to obtain a fluorinated admixture containing at least one compound of a formula $CF_2HOCH_{3-z}F_yCl_{z-y}$.

* * * * *